United States Patent [19]

Milo

[11] Patent Number: 5,704,899
[45] Date of Patent: Jan. 6, 1998

[54] PROTECTIVE SHEATH FOR A FIBEROPTIC IMAGE GUIDE WITHIN AN ARTICULATED ENDOSCOPE

[75] Inventor: Charles Milo, Union City, Calif.

[73] Assignee: Conceptus, Inc., San Carlos, Calif.

[21] Appl. No.: 541,987

[22] Filed: Oct. 10, 1995

[51] Int. Cl.⁶ ........................................ A61B 1/06
[52] U.S. Cl. .................. 600/161; 600/121; 600/123; 600/130; 600/182; 385/107; 385/144
[58] Field of Search ...................... 600/121, 123, 600/139, 140, 141, 153, 160, 161, 181, 182, 130; 385/107, 117, 144, 145

[56] References Cited

U.S. PATENT DOCUMENTS

| | | | |
|---|---|---|---|
| 4,678,274 | 7/1987 | Fuller | 385/144 |
| 4,832,444 | 5/1989 | Takahashi et al. | 600/181 X |
| 5,002,041 | 3/1991 | Chikama | 600/140 X |
| 5,263,928 | 11/1993 | Trauthen et al. | 600/182 X |
| 5,293,442 | 3/1994 | Sayegh | 385/107 X |
| 5,331,948 | 7/1994 | Utsumi et al. | 128/4 |

OTHER PUBLICATIONS

Kerin et al., *Fertil. Steril.*, vol. 54, pp. 390-400, (1990).
Kerin et al., *J. Laparoendoscopic Surg.*, vol. 1, pp. 47-56.

*Primary Examiner*—Beverly M. Flanagan
*Attorney, Agent, or Firm*—Townsend and Townsend and Crew LLP

[57] ABSTRACT

An improved endoscope prevents abrasion of a fiberoptic image guide with a braid reinforced sheath. Abrasion of fiberoptic image guides within articulating endoscopes quickly wear through a conventional fiberoptic mantle, decreasing the useful life of the endoscope. Preferably, the sheath comprises a metal braid disposed within a polyimide, which effectively protects the image guide from abrasion against the endoscope components and substantially extends useful life.

9 Claims, 1 Drawing Sheet

PROTECTIVE SHEATH FOR A FIBEROPTIC IMAGE GUIDE WITHIN AN ARTICULATED ENDOSCOPE

BACKGROUND OF THE INVENTION

1. Field of the Invention

The present invention relates generally to an endoscopic surgical apparatus, and more particularly, provides a protective sheath to prevent abrasion of a fiberoptic image guide within an articulated endoscope.

Diseases of the fallopian tubes are a major cause of infertility and tubal pregnancy. Until recently, diagnosis and treatment of tubal disease has been hampered by the difficulty in accessing and imaging the interior of the fallopian tube. Such difficulties, however, have been largely overcome by the recent availability of very small guidewires, catheters, and fiberoptic viewing scopes, usually referred to as falloposcopes. Using these instruments and systems, a physician can gain atraumatic access to the interior of the fallopian tube through a hysteroscope positioned within the uterus. Such falloposcopic imaging techniques were described by Kerin et al. in *Fertil. Steril.*, Vol. 54, pages 390–400 (1990) and in *J. Laparoendoscopic Surg.*, Vol. 1, pages 47–56.

Falloposcopic access and imaging techniques are generally performed as follows. A hysteroscope is positioned within the uterus and an irrigating solution is introduced to distend the uterus and permit video monitoring. A very small guidewire is then introduced through the hysteroscope and advance past the ostium into the fallopian tube. The guidewire will continue to be advanced until it approaches the distal fimbria. A small tubular access catheter may then be advanced through the hysteroscope and over the guidewire into the fallopian tube, again preferably approaching the distal fimbria. After removing the guidewire, the falloposcope (which is a small diameter fiberoptic bundle including both imaging and illumination fibers in a single shaft) is advanced until its distal end reaches the distal end of the access catheter. Imaging may then be performed in a retrograde manner with the falloposcope and access catheter being drawn outwardly together through the fallopian tube while producing an image on the associated video monitor. The lumen of the tubular access catheter will also provide an access path for devices, such as drug delivery catheters, small instruments, and the like, for treatment of tubal lumen disease.

In copending U.S. patent application Ser. No. 08/207,475, the full disclosure of which is herein incorporated by reference, an improved falloposcopic procedure was proposed making use of an immobilized hysteroscope. That hysteroscope included an articulated end for selectively directing a working lumen port toward an ostium of a fallopian tube from within a uterus. Accessing of the fallopian tube is performed under optical imaging provided by a lens which is oriented by the distal end of the articulated hysteroscope.

While such fallopian access and retrograde falloposcopic imaging techniques represent a significant improvement, they still suffer from certain limitations. Specifically, it has been discovered that articulating endoscopes suffer from a relatively poor reliability and a short scope life. The improved hysteroscopic and falloposcopic methods and procedures of application Ser. No. 08/207,475, as well as similar endoscopic procedures which rely on remote articulation of an endoscope, have been found to impose unanticipated demands on the optical imaging equipment. In particular, the reliability of a hysteroscope or other endoscope having an optical imaging guide which is attached to the distal end of a pullwire activated articulated tip has been found to be particularly problematic.

It would therefore be desirable to provide improved articulated endoscopes having an increased useful life. It would be particularly desirable if such improved endoscopes were compatible with retrograde falloposcopic viewing, and especially with methods utilizing an immobilized hysteroscope.

2. Description of the Background Art

U.S. patent application No. 5,331,948 describes an endoscope having a tip which is articulated by a pulling wire. An optical image guide is fixed to the distal end of the articulated tip, but is protected only by a standard mantle.

SUMMARY OF THE INVENTION

The present invention provides an improved endoscope having a fiberoptic image guide which is protected from abrasion by a braid reinforced sheath. In connection with the present invention, it has been discovered that the reliability of articulated endoscopes has been limited by abrasion of the fiberoptic image guide against the pulling wire, the articulable endoscopic sheath structure, and the other internal components of the articulating tip during articulation.

The flexibility of articulating tips is often enhanced by leaving axially oriented components within the articulating tip "free-floating." This means that axial components, such as the image guide, any illumination fiberoptics, a work conduit defining a work lumen, or the like, are not radially constrained along the length of the articulating tip, generally being fixed only at their distal ends and proximally of the articulation. Unfortunately, free-floating and other flexible structures result in sliding contact between internal components during articulation, leading to abrasion of a magnitude which a conventional fiberoptic image guide mantle is unable to withstand.

According to the principles of the present invention, an improved endoscope comprises a braid-reinforced sheath disposed over an optical image guide within an articulating tip. The sheath comprises a polymer material and a reinforcing braid to protect the image guide from abrasion. Typically, the reinforcing braid will comprise a metal such as stainless steel, or a high strength fiber such as Kevlar™, fiberglass, or the like, which is disposed within the polymer material. Preferably, the polymer material comprises a polyimide or a high strength thermoplastic elastomer such as Pebax™, Hytrel™, or the like. In a particularly advantageous embodiment, the braid is embedded within the polymer by dip-coating the braid and image guide, or by coextrusion of the braid and polymer material.

Generally, the sheathed image guide will be axially flexible within the articulating tip.

DETAILED DESCRIPTION OF THE SPECIFIC EMBODIMENTS

Figure 1:
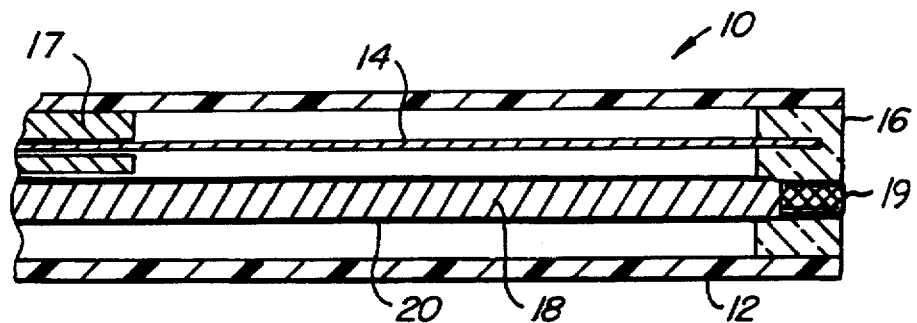
FIG. 1 is a simplified cross-section of an articulated tip of an endoscope, wherein the tip is actuated by a pulling wire, and wherein the optical image guide is protected by an sheath in accordance with the principles of the present invention.

Referring to FIG. 1, an articulating endoscope tip according to the principles of the present invention comprises a flexible sheathing tube 12 to which a pulling wire 14 is attached at a distal end 16. The proximal portion of pulling wire 14 is typically disposed within a wire guide 17, the wire guide or other structural components limiting the flexibility of the proximal portion of the endoscope. Hence, the articulating portion of endoscope 10 extends from the distal end of wire guide 17 to the distal end 16. An optical image guide 18 is also attached to the distal end of the endoscope, terminating at an imaging lens 19. Lens 19, typically comprising a GRIN lens, is thereby reoriented when sheathing tube 12 is flexed by pulling wire 14.

Figure 2:
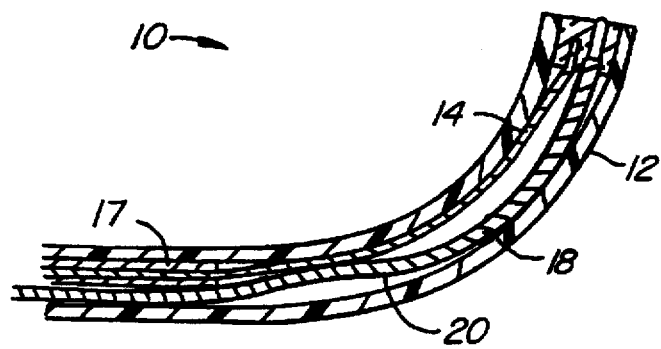
FIG. 2 is a simplified cross-section of the articulated tip of FIG. 1 which has been bent by tensioning of the pulling wire.

Referring now to FIG. 2, tensioning of pulling wire 14 compresses at least a portion of sheathing tube 12, thereby articulating the tip as indicated. Moreover, at least some of the other axial components of the articulating tip are also axially loaded in compression. This compression may lead to additional curvature of axially inelastic components, such as the image guide, as shown in FIG. 2. Regardless, as the tip bends, optical image guide 18 comes into contact with the other internal components of the endoscope, such as sheathing tube 12 and pulling wire 14. Each time the endoscope tip is articulated in this direction, the contact pattern between the image guide and the remaining internal components is repeated. To prevent abrasion of the delicate image guide at these contact points, sheath 20 is disposed over the surface of image guide 18.

Figure 3:
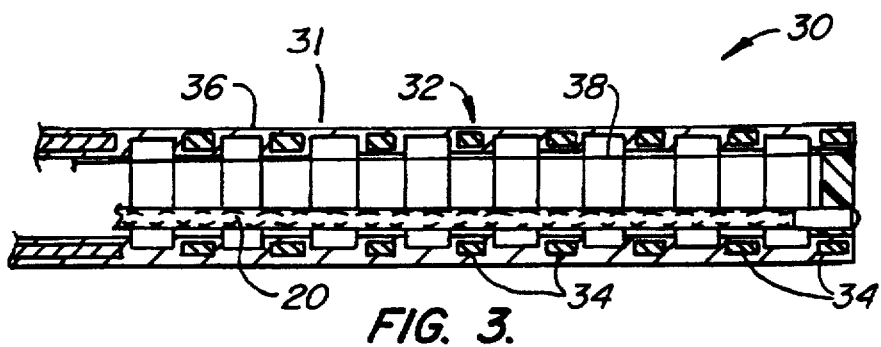
FIG. 3 is a cross-section of an articulating endoscope tip having a preferred sheathing tube cross-section.

Referring now to FIG. 3, an alternative articulated endoscope 30 includes a particularly advantageous sheathing tube 32. Sheathing tube 32 comprises a plurality of independent metal rings 34 supported by an elastomeric polymer material 36. Rings 34 maintain the cross-sectional shape of the sheathing tube, so that tension on alternative pull wire 38 evenly compresses elastomer 36 to produce a smooth curve in the distal tip. Once again, braid reinforced sheath 20 protects the image guide to prevent damage from the adjacent components within an articulated tip 31, including each of the metal rings 34.

Figure 4A:
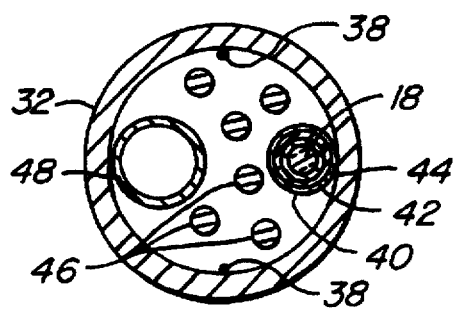
FIG. 4A is an orthogonal cross-section showing the major axial components of the articulating tip of FIG. 3.
Figure 4B:
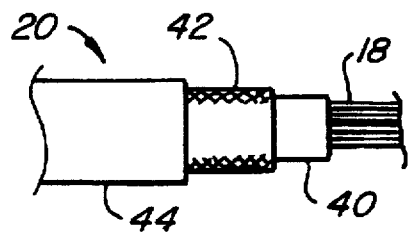
FIG. 4B is a cutaway view showing the structure of the sheath, including the outer polymer layer, reinforcing braid, and inner polymer layer, for use in the articulating endoscopes of FIGS. 1 and 3.

Referring now to FIGS. 4A and B, the internal axial components of articulated tip 31 are generally not radially restrained within Sheathing tube 32. This maximizes the flexibility of the articulating tip, and provides adequate structural integrity so long as the axial components are firmly attached at the distal end and proximally of the articulating section. The optical image guide 18 is actually composed of a large number of individual optical fibers, each typically having its own cladding. Sheath 20 comprises an inner polymer layer 40, a reinforcing braid 42, and an outer polymer layer 44. Preferably, the inner and outer polymer layers comprise a high strength polymer, such as a polyimide, in which the braid is embedded. Ideally, the polymer is coextruded with the reinforcing braid in a single process. Alternatively, the braid may be disposed over an inner polymer layer, and the assembly then dip-coated to form the outer polymer layer.

Articulated endoscope 30 also includes illumination fiberoptic bundles 46 and a working conduit 48. As described in more detail in U.S. Pat. No. 5,331,948, the full disclosure of which is herein incorporated by reference, fillumination guides 46 transmit light to the distal end of the articulated endoscope, while working conduit 48 attaches to, and has an open port on, the distal end of the articulating endoscope. These components, which are not shown in FIGS. 1 through 3 for clarity, represent additional potential contact and abrasion points for image guide 18. Additional internal components, such as dedicated irrigation or guide wire lumens, may also be provided.

Although the foregoing invention has been described in some detail by way of illustration and example, for purposes of clarity and understanding, it will be obvious that certain changes and modifications may be practiced within the scope of the appended claims.

What is claimed is:

1. An improved endoscope of the type having an articulating tip including an outer tube containing a pulling wire and a fiberoptic image guide, wherein the pulling wire is affixed to the distal end of the outer tube so that a proximal displacement of the pulling wire relative to the outer tube flexes the articulating tip, the improvement comprising:

an inner sheath disposed over the image guide within the outer tube of the articulating tip, at least an axial portion of the inner sheath and image guide being radially unrestrained within the outer tube, the inner sheath comprising a polymer material and a reinforcing braid to protect the image guide from abrasion, the reinforcing braid comprising a metal or high strength fiber.

2. An improved endoscope as claimed in claim 1, wherein the reinforcing braid is disposed within the polymer material.

3. An improved endoscope as claimed in claim 2, wherein the polymer material is coextruded with the reinforcing braid.

4. An improved endoscope as claimed in claim 1, wherein the polymer material comprises a polyamide or a high strength thermoplastic elastomer.

5. An improved endoscope as claimed in claim 1, wherein the inner sheath is formed by dip-coating an inner polymer layer and braid with an outer polymer layer.

6. An improved endoscope as claimed in claim 1, wherein the reinforcing braid comprises a metal.

7. An improved endoscope as claimed in claim 1, wherein the outer tube defines a lumen having an axis, and wherein the image guide and the inner sheath within the articulating tip are axially flexible so as to deflect laterally within the lumen of the outer tube to allow the articulating tip to flex when the pulling wire is displaced proximally.

8. An endoscope comprising:

an articulating tip having a proximal end and a distal end, the articulating tip comprising an outer tube defining a lumen, the outer tube including a plurality of metallic rings and an elastomeric material;

a pulling wire disposed within the articulating tip and affixed to the distal end;

a fiberoptic image guide disposed within the lumen of the articulating tip and having a distal lens affixed to the distal end, at least an axial portion of the image guide radially unrestrained within the lumen; and an inner sheath disposed over the image guide within the lumen of the articulating tip, the inner sheath comprising a metallic reinforcing braid disposed within a polymer;

wherein proximally displacing the pulling wire relative to the proximal end of the articulating tip flexes the articulating tip and reorients the lens, the inner sheath deflecting laterally within the lumen with the image guide during flexing of the articulating tip so that the inner sheath prevents contact damage to the image guide from contacting against at least the outer tube and the pulling wire.

9. An endoscope as claimed in claim 8, wherein the outer tube defines an axis, and wherein the image guide and the inner sheath within the articulating tip are axially flexible to allow the articulating tip to flex when the pulling wire is displaced proximally.

* * * * *